United States Patent
Vannah (10) Patent No.: US 6,201,889 B1
(45) Date of Patent: *Mar. 13, 2001

(54) APPARATUS AND COMPUTER PROGRAM FOR GENERATING A FEEDBACK CODE

(75) Inventor: William M. Vannah, Granville, MA (US)

(73) Assignee: Shriners Hospital for Children, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/099,408

(22) Filed: Jun. 18, 1998

Related U.S. Application Data (62) Division of application No. 08/777,412, filed on Dec. 30, 1996, now Pat. No. 5,771,310.
(60) Provisional application No. 60/016,178, filed on Apr. 24, 1996.

(51) Int. Cl.[7] .................................................. G06K 9/00
(52) U.S. Cl. ........................................... 382/131; 382/162
(58) Field of Search ..................................... 382/108–109, 382/128, 131–132, 141, 154, 162, 164; 348/92, 128, 65, 77

(56) References Cited

U.S. PATENT DOCUMENTS

| | | | |
|---|---|---|---|
| 4,490,913 | 1/1985 | Vis | 33/172 |
| 4,503,865 | 3/1985 | Shishido | 128/774 |
| 5,016,173 | 5/1991 | Kenet et al. | 364/413.13 |
| 5,224,376 | 7/1993 | Elings et al. | 73/105 |
| 5,226,175 | 7/1993 | Deutsch et al. | 395/119 |
| 5,372,502 | 12/1994 | Massen et al. | 433/215 |
| 5,479,024 | 12/1995 | Hillner et al. | 250/458.1 |
| 5,496,999 | 3/1996 | Linker et al. | 250/306 |
| 5,771,310 | * 6/1998 | Vannah | 382/154 |

FOREIGN PATENT DOCUMENTS

PCT/US97/05989  11/1997  (WO).

OTHER PUBLICATIONS

Boone et al., "Automated fabrication of mobility aids: Review of the AFMA process nad VA/Seattle ShapeMaker software design", *Journal of Rehabilitation Research and Development*, 31:42–49 (1994).

(List continued on next page.)

*Primary Examiner*—Bhavesh Mehta
(74) *Attorney, Agent, or Firm*—Fish & Richardson P.C.

(57) ABSTRACT

The invention features an apparatus and computer program for sampling data corresponding to a property of an object and generating a feedback code indicating the quality of the sampled data. The apparatus includes (a) an input probe for generating digital data points at a plurality of sample points on the surface of the object; (b) an output device arranged to provide the feedback code; and (c) a processor electrically connected to the input probe and the output device and arranged to analyze the digital data and provide a feedback code indicating the quality of the digital data points. The processor is programmed to (i) assign each digital data point to one of a plurality of discrete, unique compartments; (ii) determine a quality value for each of the compartments and assign to each compartment a feedback code representing the quality value; and (iii) transmit the feedback code to the output device.

20 Claims, 3 Drawing Sheets

OTHER PUBLICATIONS

Borchers et al., "Numerical Comparison of 3–D Shapes: Potential for Application to the Insensate Foot", *Journal of Prosthetics and Orthotics,* 7:29–34 (1995).

Cairns, "M+IND Announces New Method to Digitize Prosthetic and Orthotic Shapes", *M+IND Press Release,* (Nov. 5, 1996).

Horstmann et al., "Micro–Stereometry: A Frameless Computerized Navigation System for Open Microsurgery", *Computerized Medical Imaging and Graphics,* 4:229–233 (1994).

Krouskop et al., "A Computerized Method for the Design of Above–Knee Prosthetic Sockets", *Journal of Prosthetics and Orthotics,* 1:131–138 (1989).

Peters et al., "Integration of Stereoscopic DSA and 3D MRI for Image–Guided Neurosurgery", *Computerized Medical Imaging and Graphics,* 18:289–299 (1994).

Peters et al., "On–Line Stereoscopic Image–guidance for Neurosurgery", 1993 *IEEE Conference Record,* Nuclear Science Symposium & Medical Imaging Conf. 3:1805–1809 (1993).

Tan et al., "A frameless stereotactic approach to neurosurgical planning based in retrospective patient–image registration", *J. Neurosurg,* 79:296–303, (1993).

"Ultrasound Enters Third Dimension," *New Technology Week,* Nov. 20, 1995, vol. 9 No. 46.

"New Products Hand–held digitizer," *Rapid Prototyping Report,* Oct. 1, 1995, vol. 5 No. 10.

"3–D Offers New Opportunities for Imaging Growth," *3–D Ultrasound BBI Newsletter,* Feb. 6, 1992, vol. 15, No. 2.

"Prosthetics Fitting Systems", Principal Investigator: Vannier, Michael W; Washington University Sponsoring Org.: National Institute of Child Health and Human Development, FY: 95.

"ISG Technologies' Viewing Wang surgery imaging product gets FDA clearance", *The Gray Sheet* vol. 20, Issue 17, Apr. 25, 1994.

\* cited by examiner

FIG. 3

APPARATUS AND COMPUTER PROGRAM FOR GENERATING A FEEDBACK CODE

CROSS-REFERENCE TO RELATED APPLICATION

This is a divisional of U.S. application 08/777,412, filed Dec. 30, 1996, now U.S. Pat. No. 5,771,310 which claims benefit of U.S. Provisional Patent Application Ser. No. 60/016,178, filed Apr. 24, 1996.

BACKGROUND OF THE INVENTION

The invention relates to methods and apparatus for determining and recording three-dimensional ("3-D") topographies representing properties of objects.

Various systems exist that can be used to record 3-D images or topographies of surface properties of complex objects such as external human anatomic features (e.g., limbs or residual limbs), human organs (e.g., heart or brain), and skeletal structures, automobile body components, and industrial molds. For example, imaging systems such as computerized axial tomography ("CAT"), magnetic resonance ("MR"), or ultrasound imaging systems can be used to generate 3-D images of internal human structures based on X-ray, MR, or ultrasound images of "slices" of the structure. In these imaging systems, the apparatus is relatively large, and the patient lies inside the apparatus. The apparatus serves, in part, to precisely position the sensing elements. A set of two-dimensional cross-sections or "slices" are generated and the spacing from slice to slice is precisely controlled. The edges of each slice are detected, and a 3-D image is created from these edges. See, e.g., Nelson et al., "Visualization of 3D Ultrasound Data," *IEEE Computer Graphics and Applications*, 13:50–57 (1993).

Electro-mechanical systems use an electro-mechanical probe ("digitizer") to generate a digital representation of the precise locations of a multitude of points on the surface of an object, e.g., a plaster mold of a residual limb, along a prescribed, ordered path. Such systems are used, for example, in the field of residual limb shape measurement, and include the DIGITSHAPE™ (Shape Products, Ltd., W. Sussex, England, UK), and the MIND® digitizer (Model and Instrument Development, Inc.; Seattle, Wash., USA). In these systems, the object is rotated at a fixed rate, and the digitizer tip is moved along the axis of the object, also at a known rate; thus, the tip traces a precise, known helical path along the object. At each point along the path, the radial distance from the axis to the surface of the object is recorded. A 3-D image is then generated from the numerous points along the helical path. In these systems, the digitizer is positioned by a mechanism.

Digitizers which are positioned by hand have also been used to record shapes of objects. For example, the Otto Bock Shape System (Otto Bock Orthopaedic Industry of Canada, Ltd.; Winnipeg, Manitoba) uses a hand-held digitizer to record torso shape in the manufacture of custom-fit seating. The operator moves the digitizer along the surface of a mold of the torso. The operator enters a surface position sample by pressing a mouse button at operator-determined intervals. A single data point is recorded when the operator presses the mouse button, and data are recorded only when the operator presses the button. When sampling is completed, the torso shape is interpolated from these data points. Lemaire et al., *J. Rehabil. Res. & Dev.*, 33:311–320 (1996) describes this method as relatively inaccurate.

Hand-held digitizers also have been used for data entry in other imaging systems. For example, Horstmann et al., *Comput. Med. Imag. Graphics*, 18:229–233 (1994), describes an ultrasonic system for the 3-D localization of small, hand-held surgical tools used during brain surgery. The position of the tool is sent to a visualization unit and overlaid in real-time on 3-D images, e.g., CT and magnetic resonance images, of the patient's brain scanned before the operation. The main component of this system is an ultrasound transducer that indicates the precise location of a pointing device that can be attached to surgical tools.

Systems for stereoscopic image-guidance of a probe during neurosurgery are also known (see, e.g., Peters et al., *Comput. Med. Imag. Graphics*, 18:289–299 (1994), and Peters et al., "Nuclear Science Symposium & Medical Imaging Conference," 1993 *IEEE Conference Record*, 3:1805–1809 (Klaisner et al., eds., IEEE, New York, N.Y., 1993). These systems use a probe connected to a base by an articulated arm whose coordinates are constantly relayed to a computer to allow the probe to be visualized stereoscopically in 3-D images, e.g., anatomical and vascular, of a patient undergoing surgery.

Other 3-D imaging systems use a beam of light, e.g., a laser, in a regular, geometric pattern to project light with observable non-uniformities onto an object's surface. The systems detect the non-uniformities from a plurality of viewpoints, and then determine the position of the non-uniformities, e.g., by triangulation. The set of non-uniformity positions is used as a set of points to create the 3-D image of the surface of the object. Examples of such "structured" light systems include laser-triangulation systems (e.g., used in industrial measurement systems), and optical probes (see, e.g., Massen et al., U.S. Pat. No. 5,372,502 and Kenet et al., U.S. Pat. No. 5,016,173). Other light-based systems use phase-shift and Moire interference patterns. Light-based systems are restricted to the measurement of visible quantities such as surface features and color.

In other imaging systems, colors are used to represent the difference in shape between two objects. For example, Boone et al. *J. Rehab. Res.*, 31:42–49 (1994), describes the use of different colors to represent modifications to the contour of a 3-D image on a computer screen of a prosthetic socket to provide supporting or relieving forces. Borchers et al., *J. Prosthetics Orthotics*, 7:29–34 (Winter 1995), describes the use of different colors, generated after a sampling process is completed, to represent the shape differences between a foot and a shoe last.

SUMMARY OF THE INVENTION

The invention is based on the discovery that precise 3-D topographies, or maps, of various scalar properties of an object, can be easily and rapidly obtained if the 3-D topography includes a code that represents the quality of sampled data and provides a feedback signal used to improve, with additional sampling, any sampled data that is inadequate or unacceptable.

The properties of an object, e.g., a residual limb, are sampled by moving a free-floating, 3-D transducer probe (e.g., a digitizer, a digitizer combined with a transducer of an ultrasonic imaging system, or a digitizer combined with a temperature probe) on or over the surface of the object along a random path. The samples are digitized to generate a topography or map, e.g., on a computer CRT screen, of a selected property of the object. The visual map on the CRT shows at least two things, the 3-D shape (elevation) at all points sampled on the object, and a feedback code, e.g., a visual code such as color, to provide the user real-time feedback as to the quality of the data at any area of the map.

The feedback code indicates whether the data obtained at a particular location is acceptable, thus signaling the user to re-sample locations in which sampling was too sparse, erroneous, or contained excessive noise (random error). The values of properties other than elevation, e.g., temperature, are either also shown on the map or are recorded numerically in a topography file, or both.

Thus, the invention features methods and apparatus for determining and recording the 3-D topography of various scalar properties of objects. Such properties include, without limitation, surface elevation, indentation stiffness, elevation of sub-surface layers (e.g., the elevation of the surface of structures in an object, such as organs in the body), and temperature.

In general, the invention features a method of generating a three-dimensional topography of a property of an object, by (a) generating digital data points at a plurality of sample points on the surface of the object, each digital data point including a property value and a position value corresponding to a particular sample point; (b) assigning each digital data point to one of a plurality of discrete compartments based on the position value of the data point, each compartment corresponding to a unique location on the object and containing zero, one, or more digital data points; (c) determining a quality value for each of the compartments based on the quality of the digital data points assigned to that compartment, and assigning to each compartment a code representing the quality value; (d) generating and assigning new digital data points to each compartment having a code indicating an unacceptable quality value, the new data points corresponding to sample points on the object at a location corresponding to the compartment; (e) determining a new quality value for each compartment to which new digital data points have been assigned and assigning to each compartment a code representing the new quality value; (f) repeating steps (d) and (e) until all compartments are assigned a code indicating an acceptable quality value; and (g) generating from the digital data points and new digital data points a three-dimensional topography representing the property of the object.

In this method, the code can be a visual code, e.g., color, and a human operator can determine whether the code indicates an acceptable or unacceptable quality value. Alternatively, the code can be a control signal, e.g., an electrical or light signal, and a machine can determine whether the code indicates an acceptable or unacceptable quality value.

The method can further include a step of establishing a coordinate system, and/or further steps of determining whether the coordinate system has been corrupted, and establishing a new coordinate system. The method can further include a step of processing, e.g., digitally filtering, the digital data points in a compartment to remove noise.

In another aspect, the invention features an apparatus for sampling data corresponding to a property of an object and generating a feedback code indicating the quality of the sampled data. The apparatus includes (a) a probe, e.g., a transducer, for generating digital data points at a plurality of sample points on the surface of the object, each digital data point including a property value and a position value corresponding to a particular sample point; (b) an output device electrically arranged to provide the feedback code; and (c) a processor connected to the probe and the output device and arranged to analyze the digital data and provide a feedback code indicating the quality of the digital data points. The processor is programmed to (i) assign each digital data point to one of a plurality of discrete compartments based on the position value of the data point, each compartment corresponding to a unique location on the object and including zero, one, or more digital data points; (ii) determine a quality value for each of the compartments based on the quality of the digital data points assigned to that compartment and assign to each compartment a feedback code representing the quality value; and (iii) transmit the feedback code to the output device.

In this apparatus, the output device can be, e.g., a cathode ray tube or other screen, or a printer. The transducer probe can include an indentation stiffness transducer, an ultrasound transducer, a temperature transducer, or an elevation transducer. The apparatus can further include a memory arranged to store the digital data points.

In another aspect, the invention features a mechanical probe for measuring surface indentation stiffness. This probe includes a pressure chamber (maintained at either a constant or oscillating pressure by a pressure source), a piston arranged to slide freely within the chamber, wherein a distal end of the piston extends out of the chamber, a contact tip, e.g., a rolling ball in a socket, arranged on the distal end of the piston, and a position transducer attached to the contact tip. The transducer can provide a signal indicating the position and orientation of the contacting tip.

The invention further features a computer program for analyzing the quality of sampled data points representing a property of an object and generating a feedback code indicating the quality of the sampled data points, the program residing on a computer-readable medium and including instructions for causing a processor to: (a) obtain digital data points representing a plurality of sample points on the surface of the object, each digital data point including a property value and a position value corresponding to a particular sample point; (b) assign each digital data point to one of a plurality of discrete compartments based on the position value of the data point, each compartment corresponding to a unique location on the object and including zero, one, or more digital data points; (c) determine a quality value for each of the compartments based on the quality of the digital data points assigned to that compartment and assign to each compartment a feedback code representing the quality value; and (d) transmit the feedback code to an output device.

As used herein, the term "quality" when used to refer to sampled data, means the nature of the data in terms of accuracy and quantity. The quality of sampled data is low or unacceptable when there are widespread discrepancies between sampled points in a given region, and/or too few sampled points in a given region to provide a reliable representation of a property.

As used herein, the term "compartment" means a discrete, unique portion of surface area in a computer model of an object that corresponds to a discrete, unique portion of surface area of the actual object. The compartment contains values of points sampled on the surface of the object in the location corresponding to the compartment, and can be a fixed, geometric entity in the computer memory, or can be a fixed number of points from the same portion of surface area.

The invention provides several advantages. The coded, e.g., color-coded, 3-D map is available in real-time to guide the person or machine controlling the sampling process. The operator can see which surface areas of an object are sparse in sampled points, or have unacceptable samples, e.g., wide disagreement between samples; and thus can obtain further samples in these areas. In addition, the system signals corruption or disorientation of the coordinate systems of the object or transducer by a string of areas of poor quality trailing behind the current transducer position. This signal indicates the need to re-orient the coordinate systems. Disorientation of the coordinate systems is a common problem in the clinical measurement of surface properties on living human subjects.

A further advantage of the method is that areas in which the surface contour of an object is more critical can be sampled more intensely with no modification in the method, resulting in higher accuracy of the final surface contour recorded in that area. In other words, the interactive feedback code enables adaptive sampling.

The feedback code can also be used to improve the performance of noise-removal algorithms. Specifically, noise can be removed in a quality-weighted fashion, i.e., poor quality areas are heavily corrected, and high quality areas are minimally corrected. Examples of noise-removal algorithms are averaging convolutions, low-pass filtering convolutions, and least-squares fit bi-curved patches. These algorithms, while removing noise, tend at the same time to remove real features or contours of the topography. Areas where the surface contour is important are assumed to possess high quality, because these areas are sampled until high quality codes are evident. Presumably, these areas then contain an accurate record of the surface contour, and require little if any processing by a noise-removal algorithm. Therefore, the feedback code can be used as a signal to guide the amount of noise-removal required.

Furthermore, the method allows the use of continuous sampling with a hand-held, free-floating transducer/digitizer probe, which enables the method to be used on objects with unusual shapes without reprogramming or constructing a new digitizer positioning mechanism. This advantage has particular relevance when recording the unusual limb shapes encountered in pediatric prosthetics. In addition, the fact that a positioning mechanism does not surround the limb allows the space around the limb to be used for devices to secure the limb during recording of limb shape or indentation stiffness.

In general, the method inherently corrects for noisy data, and operates in an efficient and user-friendly manner in the presence of such noisy data.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention allows a surface property topography or map to be generated simply and accurately with a feedback code that allows the operator to interactively correct and improve the sampled data used to generate the map. The code, e.g., a visual code, presents information to the operator regarding the sampling already performed on the surface, thereby providing guidance for further sampling. For example, a color code can be used to represent the standard deviation of the data within each small area of the surface.
Interactive Sampling Method The primary constraint controlling applicability of the interactive sampling method is the assumption that the average value of the sampled data for a given small area converges to the "correct" value with repeated sampling, i.e., the more digital data points for a given portion of surface area, the more "correct" or accurate the resulting topography will be. This assumption implies the following corollaries. First, it implies that the data are randomly, normally distributed about the actual population mean. Second, in the case of visual feedback (i.e., versus electronic feedback in a purely automated system), it implies that the number of property fields simultaneously displayed is limited because the fields must all be readily visible to the operator. The display cannot be so complicated as to materially affect visibility of the individual fields. Thus, in principle, visual feedback works best with a single property field, that is, a scalar surface property.

Figure 1:
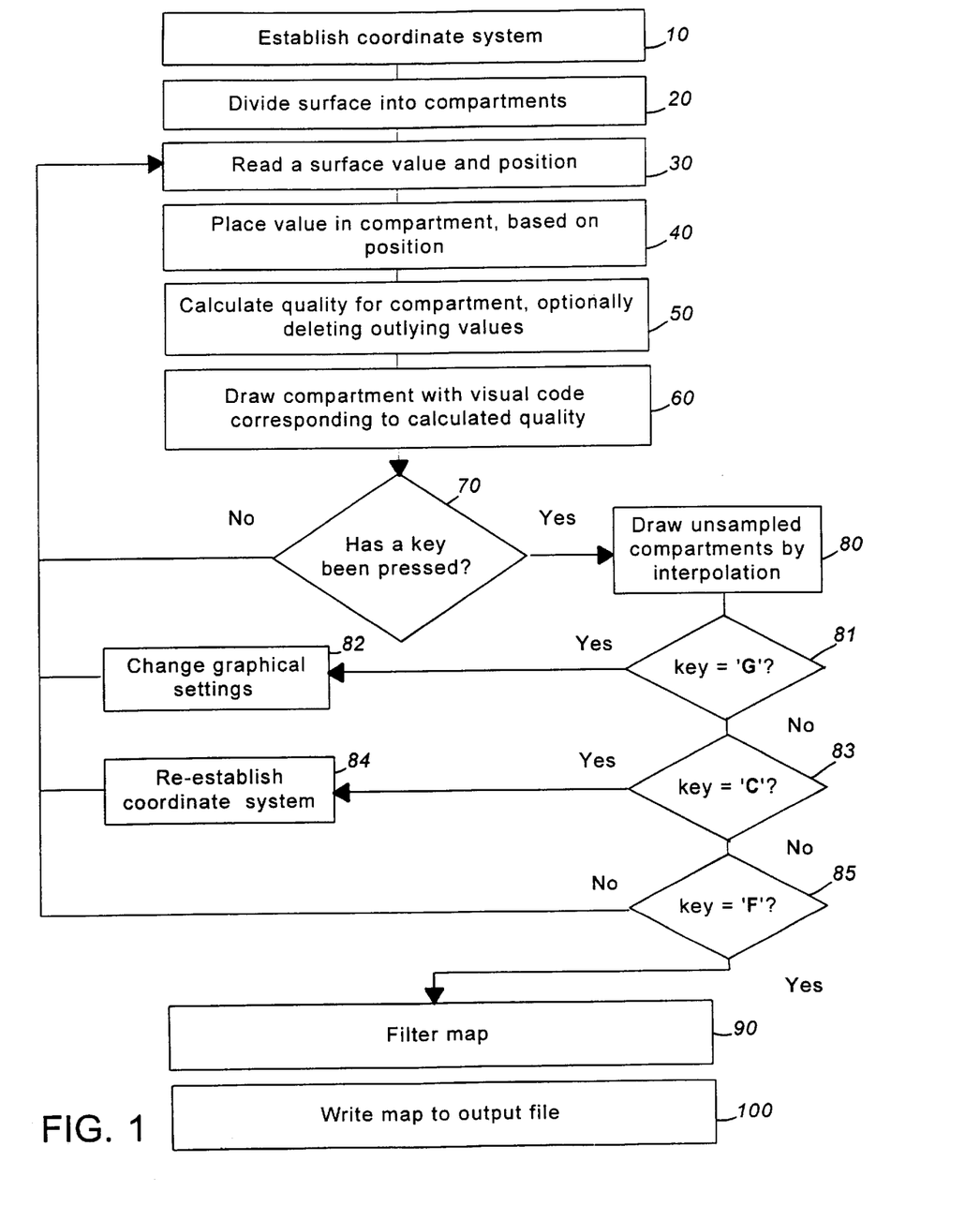
FIG. 1 is a flow chart of steps in the interactive sampling method.

FIG. 1 is a flow chart representing the steps used in the interactive sampling method. The method includes steps that can be carried out by a processor and steps that can be carried out by the operator, or a machine or robot that controls the sampling. The processor can be either a programmable computer or a dedicated processor with associated memory. Because the method operates in real time and depends on over-sampling for accuracy, processing speed affects the performance of the method. Suitable processing speeds are achieved by a Hewlett Packard (Palo Alto, Calif.) 75-mHz Vectra VL4/75, or similar computer.

In a first step 10, the system establishes a coordinate system. This can be done by digitizing several points on the object, or otherwise recording the position and orientation of geometric elements (e.g., points, lines, or surfaces) whose geometric relation to the object is fixed.

To improve efficiency, the choice of coordinate system can be based on the surface's shape. For example, the system can be established so that the surfaces of the object naturally lie along axes of the coordinate system; thus minimizing error occurring during the compartmentalization process 20 described below. The following are examples.

| Object | Suggested Coordinate System |
| --- | --- |
| rectangular box | Cartesian |
| residual lower limb | cylindrical |
| automobile fender | 2-D planar |
| mountain range | 2-D planar |
| ventricle of a human heart | prolate spheroidal |

While choosing an appropriate coordinate system can improve efficiency, many general purpose coordinate systems (e.g., the Cartesian coordinate system) can be used with sufficient accuracy if a fine compartmentalization is also used. This embodiment is particularly applicable if compartment size is based on a fixed number of points, rather than a fixed geometric area. In the case of compartments based on points, the surface can be a plane that is fit through the data points in each compartment. This allows the system to function without prior knowledge of the shape of the object, but is computationally less efficient.

Once a coordinate system is selected, the coordinate system is constructed from known geometric elements based on the nature of the data. If the position and orientation data are believed to contain errors, the position or orientation of a number of elements, e.g., points or lines, greater than that necessary to completely specify a coordinate system can be recorded (e.g., more than three ordered, non-collinear points, or more than two ordered, non-coplanar lines). The coordinate system can be established by known methods such as an error minimization method, e.g., a least-squares fit to these data points.

In a second step 20, the system divides the object's surface into a two-dimensional array of compartments. The precise manner of this compartmentalization depends on the particular object. The factors to consider in creating the correct size and number of compartments for a given object include the surface character of the object (i.e., how many undulations per surface area), the level of detail or "fineness" of the analysis, and the efficiency of the method. A compartment can contain any number of digital data points, from zero to 50 or more, but at least 5 points are preferred for sufficient accuracy.

In one embodiment, a compartment is a small 2-D area of the surface, projected in a third dimension both into and out from the object. For instance, in the case of a cylindrical object, the first two dimensions are height and included angle, and the third is the radius. Thus, for a cylindrical system, a compartment is shaped like a wedge of cheese, having a small height and angular sweep, and extending from zero to infinite radius. In the case of an elevation map of a range of mountains, the first two dimensions would be longitude and latitude, and the third would be altitude. A compartment for this example can be shaped as a four-sided column (rectangular cube) having certain small north-south and east-west dimensions, and extending vertically (in altitude) from negative to positive infinity.

The compartments can be all the same size, or they can be used as an initial step in constructing variable-sized compartments, with finer compartments used adaptively in those areas where the operator expects to sample more densely. Methods for creating variable discretization, i.e., variable-sized compartments, based on the gradient of the field to be represented are well known. See, e.g., Huebner, K. H. (ed.), "The Finite Element Method for Engineers," Third Edition (Wiley, New York, N.Y., 1995); Anand, V. B. (ed.), "Computer Graphics and Geometric Modelling for Engineers," (Wiley, New York, N.Y., 1993); Rogers, D. F. (ed.), "Mathematical Elements for Computer Graphics," (McGraw-Hill, New York, N.Y., 1990); and Baehmann et al., *J. Numer. Meth. Eng.*, 24:1043–1078 (1987).

In another embodiment, compartments are based on a fixed number of points. The compartments described above are based on fixed geometric boundaries. Thus, as samples are taken, the digital data points are assigned to these compartments, and, on average, the number of data points in the compartments increase as sampling continues. However, in compartments based on a fixed number of points, the geometric size of the compartment, on average, decreases as sampling continues.

In a third step 30, the system digitizes a surface property value (e.g., elevation, temperature, vibration amplitude or frequency, or indentation stiffness) and the position or location of a sampling point with a transducer/digitizer probe to create a digital data point, which is read and recorded. The digitizer probe continuously samples at a set rate, for example from 10 to 200 samples per second. The rate is preferably 100 to 150 samples per second. For sampling elevation of hard, non-porous surfaces, a suitable digitizer is the stylus component of the 3-SPACE® FASTRAK® system (Polhemus, Inc.; Colchester, Vt.).

For sampling elevation of softer surfaces, and for indentation stiffness measurement, a suitable digitizer probe is described below and shown in FIG. 4. The component of this digitizer that senses position and orientation is the receiver of the FASTRAK® system. Other three-dimensional digitizers also can be used to provide the required accuracy and sampling rate.

Other point-wise, three-dimensional digitizer probes are also suitable. The critical factors governing a digitizer's suitability are digitizing accuracy, digitizing rate, sampling latency, and physical size and mass. The allowable limits on these factors vary with application, but in the application of recording the shapes of molds or residual limbs, the system should have an accuracy of 0.13 mm (or less) RMS for digitizer position, and 0.15 degrees (or less) for digitizer orientation. For the same application, the digitizer system should be capable of sampling rates of 100 samples per second, and a sampling latency (time from request for data to midpoint of data transmit) of less than 10 milliseconds. Again for the same application, a preferred size is a 2 cm cube (or less), and a preferred mass is 20 grams (or less).

In a fourth step 40, the surface property value recorded in step 30 is assigned to a discrete compartment based on its recorded position. For example, if the position of the value is given in cylindrical "rθz" coordinates, the recorded "z" value will fall between the upper and lower heights for a given compartment. Likewise, the position's "θ" value will fall between the maximum and minimum angles for a given compartment. Therefore, the surface property value is assigned to that compartment. This step can occur immediately after each data point is sampled, i.e., points can be assigned to compartments in real-time, continuously rather than in batches. However, data also can be assigned to compartments in a batch mode.

In a fifth step 50, the quality of the data in the compartment chosen in step 40 is calculated. For instance, the quality in that compartment can be based on the standard deviation of the surface property values that have been assigned to that compartment thus far.

The standard deviation measure of quality can be adjusted for sparsely sampled compartments. For example, an artificially-created and large standard deviation can be substituted for compartments which contain fewer than three data points, signaling the operator that more sample points are required. The quality value can be made more accurate by assuming that certain data points in a compartment are in error ("outlying" points), and deleting or ignoring those points during calculation of a new quality value. Specifically, after calculating the mean and standard deviation of all surface property values within a compartment, each value can be examined to determine how far that particular value is from the mean. If the value falls more than some number of standard deviations ("s.d.") from the mean, for example greater than +/− 2 s.d., then the value is temporarily ignored or deleted from the compartment, and a new mean and quality value are calculated.

The quality of the data within a compartment can also be dependent on the gradient of the topography in that area, e.g., change in surface elevation. For example, areas of the topography that contain both rapid change in value and low sampling density, can be decreased in quality code. Many types of errors will result in a large gradient change. For example, if the operator inadvertently pulls the digitizer away from the surface without halting data collection, a large gradient change will occur. In this system, we assume that if large gradient changes are actual surface features, they will be heavily sampled by the operator. Therefore, the presence of both (i) a large gradient and (ii) low sampling density, implies that an error may have occurred.

Where an ultrasonic transducer is used to record the position of a sub-surface object, e.g., an internal organ, the feedback code can be modified to indicate areas where the surface is not closed. The surface closure component of the feedback code can be generated as a function of the number of free edges a compartment possesses, i.e., in full closure, each compartment has zero free edges. Generating a complete, i.e., fully closed, surface is an important task in three-dimensional modeling of internal structures. Thus, the method automatically fills unsampled areas of the topography with average values from adjoining compartments. However, this automatic filling of unsampled areas may inadvertently cause an error in the ultrasonic application, by erroneously joining adjacent organs. The error can be minimized by alerting the operator to areas where the image is not fully closed, so that further sampling can obtain a more detailed and correct image.

In a sixth step, 60, the system draws the compartment on a 3-D map, e.g., on a CRT, with the feedback code, e.g., a visual code, corresponding to the calculated quality. This is accomplished by obtaining the proper feedback code signal for each compartment from a look-up table in memory that associates particular code signals with specific quality values. In addition, the method generates a numerical or second visual topography of the object that provides a record of the values of the selected property at all sampled points on the surface of the object. This 3-D map provides the feedback code to the user to enable interactive sampling. For example, using color as a visual feedback code, and assuming error ranges typical in measuring residual limb shape with a FASTRAK® digitizer probe, the following feedback code can be used by simply having the method assign a specific color to compartments having the specific quality values (s.d. in this case) based on a look-up table as follows.

| Quality | Color |
| --- | --- |
| s.d. < 0.5 mm | dark blue |
| 0.5 mm <= s.d. <= 1.0 mm | light blue |
| 1.0 mm <= s.d. <= 1.5 mm | gray |
| 1.5 mm <= s.d <= 2.0 mm | red |
| 2.0 mm <= s.d. <= 5.0 mm | pink |
| <3 points in compartment | pink |
| s.d. > 5.0 mm | white |
| no points in compartment | white |

The visual code can also be represented by gray-scaling, or by various other visual means (stippling, striping, circles, etc.). The correlation between quality and the visual code, e.g., color, can be adaptively altered so as to improve system performance. For example, as sampling is continued, visual differences can be crowded towards the higher-quality end of the scale to allow finer work. This can be accomplished by resetting the look-up table to change the code scheme to be based on a finer standard deviation.

Additionally, shading can be employed to provide the flat CRT image with a 3-D appearance, thus alerting the user to misshapen, and therefore presumably poorly sampled, areas of the surface. The shading is done by calculating the image intensity for a given compartment as a function (e.g., cosine) of the angular orientation of the surface at that compartment to a given light source direction.

When a visual feedback code is used, the number of property fields that can be simultaneously displayed is limited due to the requirement that each field be readily visible to the operator. Visual display of more than one field of properties simultaneously can be accomplished by using multiple overlaid images; for instance, a gray scale image for one property, a color image for a second, and graphical features for a third, e.g., stippling, where density of stippling is proportional to the quantity displayed.

In a seventh step 70, the system queries whether the user has pressed a key, e.g., on a data entry board. This feature allows the user to perform several alterations in the program described below. If no key is pressed, the system begins sampling again at step 30. This step or feature is preferred when the operator is a person, but not required for the basic interactive sampling method. For example, in an automated system, the method can determine whether the coordinate system has become corrupted by analyzing the last points, e.g., five points, added to a compartment, and determining whether they exhibit a sudden change in quality value. A sudden deterioration indicates a corruption of the coordinate system, which can then be re-established as described below (step 84).

If a key has been pressed, the system first draws any unsampled compartments onto the image on the CRT screen by interpolation based on property values from adjacent compartments (step 80), and then takes further action depending on which key was pressed. Specifically, the unsampled compartments are assigned mean property values by methods known in the fields of numerical analysis and computer-aided design, e.g., "curve-fitting" or "patch-fitting." See, e.g., Babuska et al. (eds.), "Accuracy Estimates and Adaptive Refinements in Finite Element Computations," (John Wiley, Chichester, United Kingdom, 1993); Bartels et al., "An Introduction to Splines for Use in Computer Graphics and Geometric Modeling," (Morgan Kaufmann, Los Altos, California, USA, 1986); Dierckx, P., "Curve and Surface Fitting with Splines," (Oxford Scientific, Oxford, 1993); Huebner, K. H., supra; Anand, V. B., supra; Rogers, D. F., supra; and Baehmann et al., supra.

For example, the system can fit bi-curved splines through the property values in compartments surrounding the unsampled compartment, thus allowing calculation of a substitute mean value for the unsampled compartment. The number of adjacent compartments included in the calculation can be governed by the density of the sampling in that local area. For instance, the number of adjacent compartments sampled can be increased until the total number of samples in all the compartments used for the interpolation exceeds some set number, for example, 100 samples.

Further, the interpolation can be weighted by the quality of samples in each compartment, with higher quality compartments carrying greater weight. The density-weighted convolution discussed in step 90 gives an example of this type of interpolation.

Once property and quality values have been assigned to each compartment, including all compartments with no sampled data points, the object is redrawn on the CRT. For compartments in which no samples were available, a "dummy" visual code corresponding to a low quality is assigned; other compartments can use the visual code calculated based on the samples within them as described in step 60. Once the object is redrawn, the next action of the system is governed by the identity of the key that was pressed.

If the key pressed was "G" (or some other specific key)(step 81), the system stops sampling to allow the operator to change graphical settings (step 82). For example, if the system is configured so that the CRT image is opaque, then only approximately half of the surface is visible from any viewpoint, and thus the system can allow the viewpoint to be rotated about an axis through the image.

Other configurations can be used. For example, if the system is used to generate a 3-D solid shape of an underlying skeletal structure from a serially-sampled set of edges detected from 2-D ultrasonic sampling, the operator can change between images showing those compartments that contain sample data points, and those that do not (otherwise, those which are sampled will visually mask those which are not). Further, if the image is translucent, so that the back half of the object's surface is partially visible, the levels of translucency can be adjusted. Still further, the operator may want to zoom in or out on various areas of the surface. Also, the operator may want to change the position of the light source for shaded 3-D shape viewing. Finally, the operator may wish to adjust the settings of the visual code. After the settings have been changed, the object is redrawn (step 80 is repeated), and the system returns to step 30 to begin sampling again.

If the key pressed was "C" (or other specific key) (step 83), the system stops sampling and allows the operator to re-establish the coordinate system by again digitizing several points on the object (step 84). Thus, the actions described in step 10 are repeated. However, although the coordinate system is reestablished, the compartments are not changed. That is, the height of the object and the number of slices comprising that height are not changed, and the compartments continue to represent the same discrete portions of the surface area of the object. Moreover, previous sample data points remain in the compartments to which they were originally assigned.

The only effect of re-establishing the coordinate system is to change the position of the origin and orientation of the axes of the measurement coordinate system versus the ground coordinate system of the digitizer. After the coordinate system is re-established, the system again begins sampling (step 30).

If the key pressed was "F" (or some other, different, specific key) (step 85), the system leaves the sampling loop, and proceeds to step 90. Note that this step requires that the operator, or some automated machine, make a decision that the quality everywhere on the map is sufficient for a given purpose. This step 85 can also be accomplished without a keystroke, i.e., the system can determine that all compartments meet required quality values and provide a signal to the operator, or an automated sampling probe, that sampling is complete.

If the key pressed is other than one of the defined keys, e.g., G, C, or F, the system by default returns to sampling again at step 30.

In step 90, the map of mean values in each compartment may be, at the operator's option, processed to remove noise (randomly-distributed error) in measurement of the surface values. These processes can include various spatial convolutions commonly known in the field of digital signal processing, various known patch-fitting techniques, and modifications of these known methods to allow use of the quality feedback code. The convolutions can include smoothing filters, median filters for noise reduction, low-pass filtering, and edge detection filters. See, e.g., Castleman, "Digital Image Processing" (Prentice-Hall, Englewood Cliffs, N.J., USA, 1979); Glassner (ed.), "Graphics Gems" (Academic Press, Boston, Mass., 1990); Arvo, J. (ed.), "Graphics Gems II" (Academic Press, Boston, Mass., 1991); Kink, D. (ed.), "Graphics Gems III" (Academic Press, Boston, Mass., 1992); and Jahne, B. (ed.), "Digital Image Processing," (Springer-Verlag, New York, N.Y., 1991). Patch-fitting methods have been discussed in step 80.

A novel feature of the method is that these noise-removal processes can weight a given compartment's contribution to the convolution as a function of the feedback code, e.g., quality feedback code, of that compartment. The result of this weighted processing is that poor quality areas of the surface are more heavily-processed, and high quality areas of the surface are virtually unaffected. This is advantageous because processing, while removing noise, can also erroneously smooth out real contours of the surface property value map, removing information. For instance, compartment quality can be used to set pass frequency in low-pass filters; that is, areas of poor quality can be filtered at a very low frequency, thus smoothing the contours. Areas of high quality can be filtered at a higher frequency, thus removing only those surface oscillations known to be above any actually occurring in the surface. In the case of typical residual lower limbs, the preferred upper limit to actual surface oscillation is believed to be about 4 to 10 cycles in a distance equivalent to one limb circumference. The quality feedback code can also be used to adjust the extent of adjoining compartments used in an averaging convolution; as detailed below.

Again, in areas on the surface where accurate information on a fine scale is important, the operator samples many times, continuing until the system provides a feedback code indicating very high quality. Therefore, each compartment corresponding to the important areas of the surface contains many samples from which to calculate a mean surface property value; thus, any random noise occurring during sampling is greatly diminished. That is, the method assumes that the mean value for a compartment converges to the "correct" value with increased sampling. Therefore, densely sampled areas tend not to need filtering.

Conversely, in areas where the surface shape is relatively unimportant, the operator can sample lightly and quickly, saving time and effort. In these sparsely sampled areas, random noise may greatly affect the surface map contours; however, filtering can smooth the contours. For example, the shape of the residual limb at thinly-padded bony prominences (e.g., patella, tibial crest, or shin) is very important in sockets for artificial limbs. On the other hand, the shape of muscle bellies (e.g., the calf) is less important (as long as volume is conserved). Thus, the adaptive sampling enabled by the interactive sampling method also allows improved filtering methods, because the filtering can be weighted inversely on the sampling density.

As an example, the following describes (i) unweighted, (ii) uniformly-weighted, and (iii) sampling density-weighted filtering. One method of filtering a 2-D matrix of surface property values ("data matrix"), is to replace each value of the matrix by the average of that value and its surrounding 8 values (unweighted filtering). For instance, if the matrix is:

| 3 | 2 | −1 |
| 2 | 5 | 3 |
| −6 | 0 | 1 | then after the filtering operation is applied to the value in the central position (i.e., 5) of the matrix, the new value in the central position is:

$(3+2-1+2+5+3-6+0+1)/9=9/9=1$

After this single step of the filtering operation, the data matrix would be:

|   |   |    |
|---|---|----|
| 3 | 2 | -1 |
| 2 | 1 | 3  |
| -6| 0 | 1  |

Of course, in actual practice, the method would filter all members of the matrix. This operation is frequently described in abbreviated notation by the left-hand matrix below:

|   |   |   |     |   |   |   |
|---|---|---|-----|---|---|---|
| 1 | 1 | 1 |     | 1 | 1 | 1 |
| 1 | 1 | 1 |     | 1 | 3 | 1 |
| 1 | 1 | 1 |     | 1 | 1 | 1 |

The left-hand matrix denotes an unweighted, averaging or smoothing 3×3 filter ("filter matrix"). The right-hand matrix is also a 3×3 smoothing filter matrix, but more heavily weights the contribution of the original value in the central position of the data matrix. This is uniformly-weighted filtering. If the right-hand filter matrix is applied to the original data matrix, the operation would be:

$$[(3\times1)+(2\times1)+(-1\times1)+(2\times1)+(5\times3)+(3\times1)+(-6\times1)+(0\times1)+(1\times1)]/9 = 19/9 = 2.11$$

which could be rounded to 2. After this single step of the filtering operation, the data matrix would be:

|    |   |    |
|----|---|----|
| 3  | 2 | -1 |
| 2  | 2 | 3  |
| -6 | 0 | 1  |

In practice, all members of the data matrix would be filtered, and only the central value is filtered here to simplify the example.

In practical terms, the difference between the results of left- and right-hand filter matrices (above) is that the right-hand matrix would not filter as heavily.

To apply this general filtering method to a specific example, e.g., to a map of residual limb mold elevations, a data matrix of values is created in which each value is the average of the elevations found in a given compartment. The matrix includes all compartments and is thus much larger than a 3×3 matrix, but the filter matrix would be used in a manner identical to that presented above.

Sampling density-weighted filtering contains elements of unweighted and uniformly-weighted filtering, with the following differences. To create a sampling density-weighted filter, the data matrix is changed slightly to include for each member both the average property value of the compartment, and the number of data points in that compartment. Thus, a 3×3 section of the data matrix might be:

|       |       |        |
|-------|-------|--------|
| (3,4) | (2,6) | (-1,5) |
| (2,7) | (5,9) | (3,4)  |
| (-6,4)| (0,6) | (1,5)  | where the "(#, #)" notation implies that the first member of the data matrix has an average elevation of 3, based on 4 data points, the second member has an average elevation of 2, based on 6 data points, and so on. The sample density-weighted filtering operation would then replace the central value of the data matrix, using the right-hand filter matrix above, as follows:

$$[(3 \times 4 \times 1) + (2 \times 6 \times 1) + (-1 \times 5 \times 1) + (2 \times 7 \times 1) + (5 \times 9 \times 3) + (3 \times 4 \times 1) + (-6 \times 4 \times 1) + (0 \times 6 \times 1) + (1 \times 3 \times 1)] / [4 + 6 + 5 + 7 + 9 + 4 + 4 + 6 + 5] = 161 / 50 = 3.22$$

which could be rounded to 3. The data matrix of elevations would then be (leaving off the number of data points):

|    |   |    |
|----|---|----|
| 3  | 2 | -1 |
| 2  | 3 | 3  |
| -6 | 0 | 1  |

Again, noting that in practice all members of the data matrix would be filtered.

The filtering operation also can be performed to obtain identical results by simply adding the values of all of the individual data points present in all compartments of, e.g., a 3×3 portion of the data matrix, and dividing by the number of data points in that portion.

A second density-weighted method is to use the number of data points in the compartment corresponding to the central matrix value for the filter matrix, and use 1 (or some other fixed value) for the other values in the filter matrix. That is, for the example here, the filter matrix would be:

|   |   |   |
|---|---|---|
| 1 | 1 | 1 |
| 1 | 9 | 1 |
| 1 | 1 | 1 | where the value 9 results from the fact that there are 9 values in the compartment corresponding to the central value of the data matrix. These examples can be expanded and modified to cover a wide variety of noise-removal processing required for the interactive sampling method.

After noise-removal step 90, the map of surface property values is output (step 100), e.g., by saving to RAM, diskette, or paper printout of the mean surface property quality value in each compartment.

Generating 3-D Topographies

The interactive sampling method can be used to easily obtain and record precise 3-D topographies of the body for use in medicine, e.g., images of external limbs or residual limbs, internal organs, and skeletal structure. For example, in combination with a digitizer, an ultrasound transducer system (e.g., the Shimadzu SDU-500, Shimadzu Corp., Kyoto, Japan) becomes a 3-D shape recording system. The boundaries of various organs can be defined on 2-D images by edge-detection convolution; then these edges can be joined together to form a 3-D closed surface. Moreover, the method can be used interoperatively to record the 3-D shape of an external or internal body structure before and after a surgical procedure to judge the accuracy and effect of that procedure.

The method can also be used in non-medical applications which require a precise 3-D topography of an object. For example, the method can be used in industrial mold making, tolerance testing of auto bodies, and mapping of geographic features such as mountains. In these methods, the feedback code on the image can be a visual code for a human operator, or an electrical signal used to instruct a machine, e.g., a robot, that controls the positioning of the transducer/digitizer probe that obtains the data samples.

3-D Mays of Residual Limbs

In one embodiment the interactive sampling method can be used to generate 3-D maps and topographies of residual limbs to design properly fitting prosthetics. The interactive sampling method can be used with any CAD/CAM equipment for designing prosthetics and orthotics. Current residual limb imaging systems require precise positioning mechanisms for the digitizer probes. The interactive sampling method allows these existing positioning mechanisms to be replaced by a free-floating (i.e., hand-held) transducer/digitizer probe and a programmed computer.

The basic method of digitizing a residual limb, sculpting a 3-D computer image of the limb to fit an acceptable prosthetic socket, and then creating a socket based on a computer-carved solid model of the socket is well known in this field. See, e.g., Boone et al., *J. Rehabil. Res.*, 31:42–49 (1994). However, in this known method, the residual limb is digitized with an electro-mechanical device that is moved along the axis of a cast of the limb at a fixed rate, and the cast is rotated at a fixed rate. Thus, the digitizer probe traces a precise, known helical path along the object. A 3-D image is then generated from the numerous points along the helical path.

The interactive sampling method enables the user to obtain an accurate 3-D image of the residual limb without the need for the cumbersome positioning mechanism, and without the need for a precise, pre-defined path for the transducer/digitizer probe. The suggested method to record the surface shape of a prosthetic socket is as follows. A coordinate system is first established by picking three points on the limb with a hand-held, free-floating 3D digitizer (e.g., a 3SPACE® FASTRAK®, Polhemus, Inc., Colchester, Vt.).

Residual limbs are generally shaped like a cylinder, thus a cylindrical coordinate system is chosen, with the vertical axis approximately coincident with the natural vertical direction of the limb during stance. Three points on that cylinder are digitized; the first is at the center of the bottom of the cylinder (distal-central), the second is at the top and rear-most aspect of the cylinder (proximal-posterior), and the third is at the top and front-most aspect (proximal-anterior). The origin of the coordinate system is established at the first point. The vertical axis of the coordinate system is then established to run from the first point, through a point that is the average (or midpoint) of the second and third points. The zero degree radial axis (commonly called the "θ" or "theta" axis) is established from the origin radially outwardly in the direction of the third point.

After a coordinate system is established, the residual limb is compartmentalized within this coordinate system in a computer memory or database. Compartments for this embodiment are generated as follows. The vertical dimension of the limb is segmented into slices, based on the height of the limb (determined from the three previously-digitized points) divided by some predetermined slice thickness, e.g., five millimeters. Each slice is then segmented into compartments with some predetermined angular dimension, for example, 0.1 radians, so that the resulting compartments are shaped like a wedge of cheese in 3-D. A two-dimensional array of 3-D compartments is defined, where each compartment represents a wedge-shaped volume of the space occupied by the limb, five mm high and 0.1 radians in angle and extending radially outward from radius=0 to radius=∞.

To determine elevation, the surface of a solid cast of the limb is then sampled by moving the transducer/digitizer probe over the surface along a random path and continuously recording data of sample point position at a rate of, for example, 120 samples per second. The digital data points are recorded in the corresponding discrete compartments in the computer memory. To determine indentation stiffness, a probe as described below is moved across the surface of the actual residual limb.

As the sampled data points are recorded, an image or map of the surface is created on a CRT. The color of small, discrete areas of the image is defined to represent the quality of the sampled data in that area. The position of each compartment in the 3-D image on the CRT is defined by the average of position values, e.g., average radius, of the data points within that compartment. The quality for an area can be a function of the standard deviation of the samples taken in that area. Samples more than some chosen number of standard deviations away from the current average for a given area (for example, >±2 s.d.) are temporarily eliminated, and a new average, standard deviation, and color are calculated.

Areas in which no samples are taken are given the average value of nearest neighbors by interpolation as described above, and are assigned a color code implying a "dummy" high standard deviation. The surface can be more heavily sampled in those areas of the socket in which a more accurate fit is known to be important; for example, in the areas of thinly-padded bony prominences.

The image of the object should be shaded (the image intensity should be varied) based on the angle between the surface at any point and a selected light source position. Such a shading scheme provides the operator with a 3-D view of the map. Poorly-sampled areas of the map can be noted and corrected (with further sampling) by observing misshapen areas.

Finally, if the orientation of the coordinate systems of the object and transducer become corrupted, this corruption is evident in that a string of areas of poor quality color appears, trailing behind the current transducer position, thus indicating the need to re-orient the coordinate systems. Disorientation of the coordinate systems is a common problem in the clinical measurement of surface properties on living human subjects.

Figure 2:
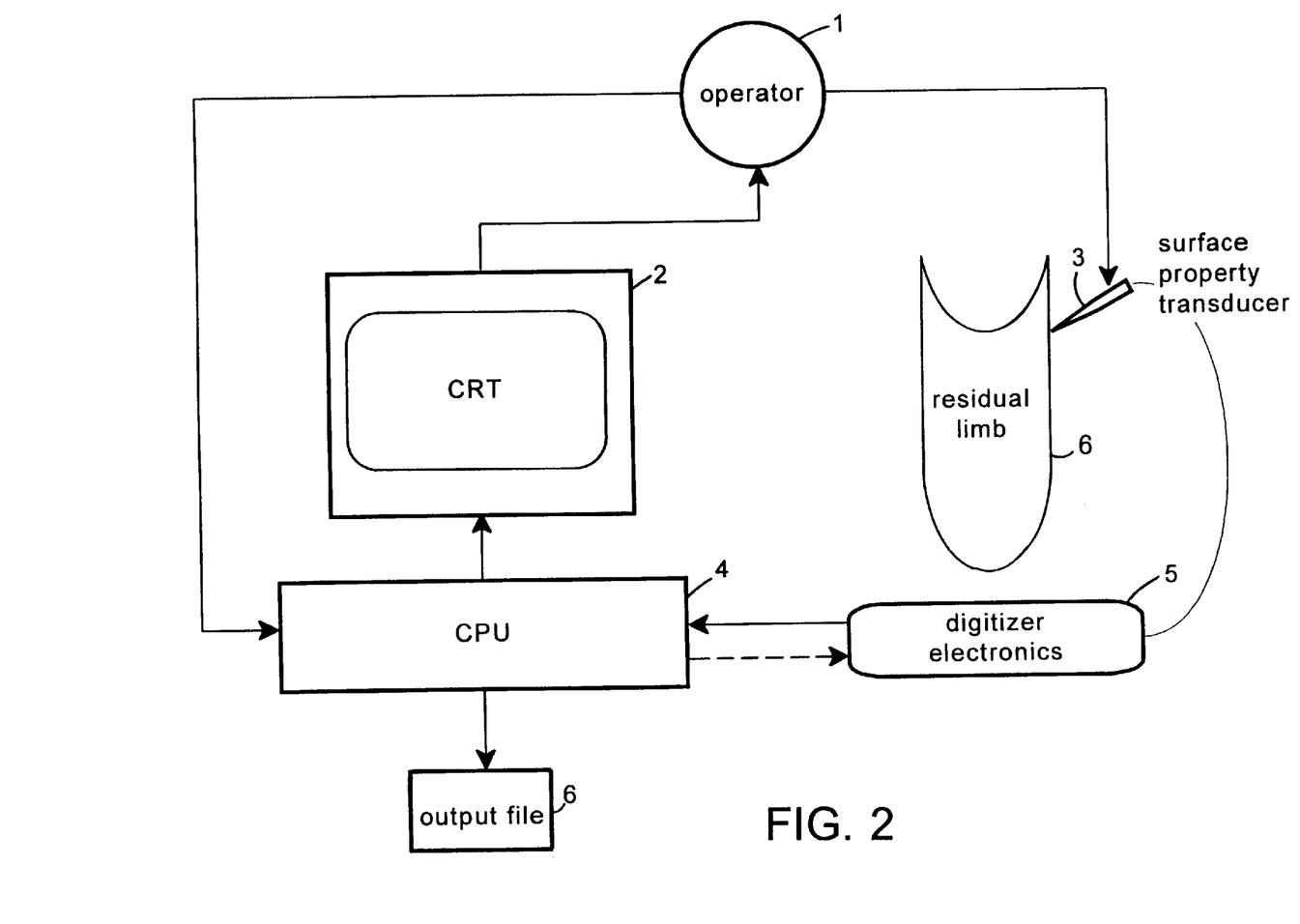
FIG. 2 is a control system diagram of a residual limb topographical 3-D imaging system.

FIG. 2 is a control diagram of a residual limb topographical 3-D imaging system. The operator 1, receives information by observing the coded image of the object as it appears on the CRT display 2. Based on this coded image, the operator moves the transducer 3 to sample areas of the residual limb 6 which need further sampling.

As surface property value data points are recorded by the transducer 3, the transducer and digitizer electronics 5 also record the position and orientation of the transducer corresponding to each surface property value. The digitizer electronics 5 convert these analog values to digital format and present the data points to a buffer in the CPU 4. The CPU 4 and accompanying logic program then reads the surface property and position/orientation data, and, with control from the operator 1, performs the steps described above and illustrated in FIG. 1. In particular, the CPU 4 writes the object's shape and feedback code to the video memory of the CRT 2, so that these images can be observed by the operator.

In the case of automated mechanized control of transducer/digitizer probe position, the feedback signal is transmitted directly to a control system within operator 1. Once all areas of the image are of acceptable quality, the operator 1 signals the CPU 4 to write an output file 6 containing the comprehensive surface property value and quality value map.

3-D Mass of Internal Body Structures

When combined with a position and orientation transducer and a computer programmed to perform the interactive sampling method of the invention, a 2-D ultrasound imaging system can record 3-D internal body structures. For example, the system can be used to record the surface shape (topography) of an underlying skeletal structure from a serially-sampled set of edges detected by 2-D ultrasonic sampling. This embodiment can be accomplished as follows.

The ultrasound system used must be capable of producing 2-D gray-scale images in real-time, i.e., at least 10 frames/second. A suitable ultrasound transducer is the Shimadzu SDU-500B (Shimadzu Corp, Kyoto, Japan). A high-speed, high-accuracy 3-D position and orientation transducer (e.g., the receiver of the 3-SPACE® FASTRAK® digitizing system; Polhemus Corp., Colchester, Vt.) is attached to the ultrasonic transducer.

The transducer probe is moved, e.g., by hand, along a limb or body portion with 2-D gray-scale images being continuously generated by the ultrasound transducer. It is not necessary, nor is it desirable, for the 2-D images to be mutually parallel, as is commonly the requirement in tomography. These 2-D images are read into a CPU using a high-speed video capture circuit board (e.g., DT-3152; Data Translation Corp., Marlborough, Mass.), and are then processed in real-time to detect edges using well-known edge-detection methods. After the boundaries of various organs are defined by edge-detection convolution, the boundary edges can be joined together to form a closed surface. See, e.g., Castleman, supra; Glassner, supra; Arvo, supra; Kink (ed.), "Graphics Gems III," supra; and Jahne, supra; Stand, "Ultrasonic Image Data for Prosthetic Socket Shaping," (Senior Thesis, School of Engineering, Western New England College, 1996).

Ultrasound-images are inherently noisy; thus the multiple-sampling, feedback and noise-correcting features provide an advantage in generating a smooth, high-accuracy image. In this embodiment, the quality feedback code should be modified to alert the operator (or operating mechanism) of areas where the surface is not closed. For a given compartment, this can be done by counting the edges that do not have adjoining compartments. Openings in the surface are therefore identified by compartments that are not fully surrounded, and these compartments should have their quality code adjusted (e.g., by additional sampling).

The detected edges are those at the interface between soft tissue and bone; this interface produces the strongest reflection, and thus these edges are easily differentiated from other edges. The location of the bone edges relative to the ultrasound transducer is thus known from the 2-D image. The location of the ultrasound transducer, and its 2-D image, is known relative to the coordinate system of the limb based on information provided by the position and orientation transducer attached to the ultrasound transducer. Thus, the location of these edges in the coordinate system of the limb is known.

Each digital data point representing a sample point on an edge thus represents a point on the surface of the skeletal structure, and is subsequently treated in a manner identical to that already described herein for data points taken during recording of the shape of a mold of a residual limb. That is, for the example of a cylindrical coordinate system, each point is placed in a compartment based on the point's geometric position; then the mean radius and quality of the data points within each compartment are presented to the operator via a coded image.

Ultrasonic imaging and edge-detection are both noise-prone, thus the benefit of the method in correcting noisy data is especially important. The interactive sampling method avoids the problems of noisy data by enabling the operator to oversample specific areas, by signaling the operator which areas have poor quality data and require additional sampling, and by allowing the system to discard outlying data points.

In some cases, only the outside edge of a skeletal structure can be recorded with this embodiment; i.e., multiple bones lying in close, overlapping proximity (e.g., the tarsals) cannot be individually imaged. Instead, the system records the shape of the outside of the group of bones. However, if the shapes are cleanly separated, two or more surfaces can be simultaneously recorded with this embodiment by the use of translucent images.

For example, the external limb shape can be recorded simultaneously with the shape of the underlying bone structure. In this embodiment, the limb is immersed in a tank of water, along with the ultrasound transducer, to acoustically couple the limb segment and transducer. The transducer is then moved by hand through the water over the surface of the limb, with 2-D gray-scale images being continuously generated by the ultrasound transducer. These images are then read into the CPU and two edges are detected. These two edges are the water/soft tissue interface, and the soft tissue/bone interface. Two edges are detected, and topographies of two surfaces are generated simultaneously.

This embodiment also can be used to record the shapes of non-bony internal structures (i.e., soft tissues), by re-tuning the ultrasonic system and standard edge detection algorithms. Moreover, the ultrasound transducer embodiment can be used on non-biological objects.

In another example, the interactive sampling method also can be used to generate solid 3-D topographies from serially-recorded 2-D images (as opposed to representing only the surface shapes of internal structures). Such solid 3-D topographies can be generated by presenting, e.g., on a CRT, only those areas of the object that have been poorly or inadequately sampled; i.e., by presenting a visual code in which areas of high quality are not visible. Thus, only those locations within the object that require further sampling are visible to the operator on the 3-D map on the CRT. The outside edge of the object is made visible (which is necessary for sampling) by presenting those points on the surface in a pale translucent visible code, and internal, poor quality sample locations are represented by a bright, easily-visible, color code. For instance, in the case where a cylindrical coordinate system is used, those points with greatest radius are presented in a translucent visible code on the map to show the 3-D surface.

Digitizer Probes

Various probes can be used with the interactive sampling method to record different types of property values of an object. For example, a simple rod attached to a known digitizer, e.g., the receiver of the 3-SPACE® FASTRAK® digitizing system (Polhemus Corp., Colchester, Vt.), can be used to record the surface elevation of an object. As described above, an ultrasound probe combined with a known digitizer receiver can be used to record the surface elevation or solid 3-D structure of internal body structures. Furthermore, an indentation stiffness probe can be used to generate a map of the resistance to pressure of all areas on the surface of an object, such as a residual limb.

Figure 3:
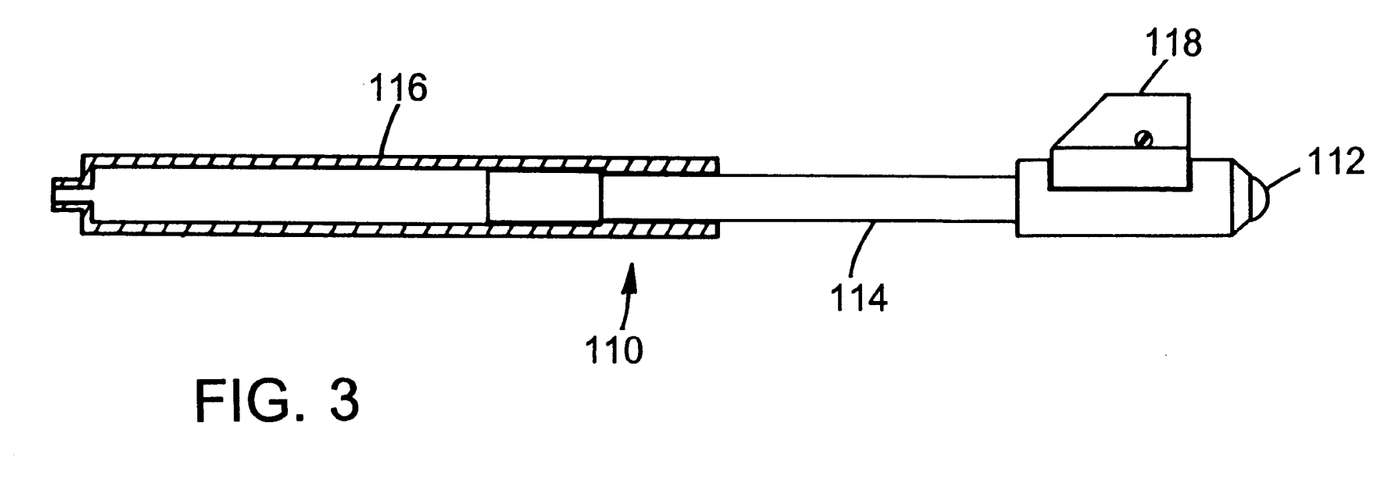
FIG. 3 is a schematic diagram of an indentation stiffness digitizer probe.

For example, FIG. 3 shows a probe 110 that can be used to measure indentation stiffness of an object. The probe includes a handle/pressure chamber 116, a piston moving freely within the pressure chamber, and a roller ball tip 112 attached to the distal end of the piston 114. The probe also includes a position and orientation transducer such as the receiver of the 3-SPACE® FASTRAK® digitizing system.

In use, piston 114, and thus roller ball tip 112, is driven outwards with a small constant force by pressure in the handle/pressure chamber 116. This pressure ranges from a low force sufficient to create a pressure of 0.5 Newtons on a 10 mm diameter roller ball tip (e.g., 0.5 psi), to a high force sufficient to create a pressure of 5.0 Newtons. The constant pressure is provided, e.g., by a pressurized air or other fluid supply (not shown) that fills pressure chamber 116 with pressurized air. Other means of providing constant pressure are known.

The operator grasps the probe by the handle/pressure chamber 116 and moves the probe over an object, e.g., a residual limb, holding the probe roughly normal to the surface. The roller ball tip 114 is urged against the surface of limb by the constant pressure on piston 114. The adequacy of the sampling in each area is judged by the feedback code.

If the pressure in the handle/pressure chamber 116 is held at a constant value, the indentation force is constant. The position of the roller ball tip 112 at any time is known because the tip has a fixed geometric relationship with the position and orientation transducer 118. Thus, an elevation map of the limb is generated where the elevation at each point is not the undeformed shape of the limb, but is instead a record of the indentation of the limb at that point which would occur under the given force.

A linear indentation stiffness topography can be generated by subtracting the difference between two elevation maps; one recorded using a very low chamber pressure (e.g., 0.5 psi), and a second recorded at a higher chamber pressure (e.g., 10.0 psi). A non-linear indentation stiffness topography requires more than two elevation topographies.

Alternatively, a pressure that oscillates rapidly between high and low pressure can be used to generate either a linear or non-linear indentation stiffness topology. In this case, the indentor itself oscillates, and indentation can be calculated directly as the difference between the most recent minimum and maximum positions of the indentor tip. Further, if a sufficiently rapid oscillation rate is used, for example, 10 or 12 Hz, effects of subject movement can be largely canceled out. Inadvertent subject movement is a common problem in recording geometric data from living subjects.

When the oscillating indentor method is used, the indentation (calculated as the difference between most recent minimum and maximum positions of the indentor tip) is the surface property value whose quality is used as the feedback variable. The maximum positions of the indentor tip can be used at the same time to provide an estimate of the exterior shape of the limb, which is necessary for the CRT graphic display.

Oscillating pressure can be easily achieved by providing a calibrated air leak in the indentor body, and cutting off the air flow to the indentor body in a regularly periodic manner. Other means of achieving oscillating pressure are known; for instance, connecting the air line to a chamber with a reciprocating piston.

Implementation

The invention can be implemented in hardware or software, or a combination of both. The interactive sampling method can be implemented in computer programs using standard programming techniques following the method steps and figures described herein. The programs should be designed to execute on programmable computers each comprising a processor, a data storage system (including memory and/or storage elements), at least one input device, and at least one output device, such as a CRT or printer. Program code is applied to input data to perform the functions described herein and generate output information. The output information is applied to one or more output devices such as a CRT, as described herein.

Each program is preferably implemented in a high level procedural or object oriented programming language to communicate with a computer system. However, the programs can be implemented in assembly or machine language, if desired. In any case, the language can be a compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An apparatus for sampling data corresponding to a property of an object and generating a feedback code indicating the quality of the sampled data, said apparatus comprising
   (a) an input probe for generating-digital data points at a plurality of sample points on the surface of the object, each digital data point comprising a property value and a position value corresponding to a particular sample point;
   (b) an output device arranged to provide the feedback code; and
   (c) a processor electrically connected to said input probe and said output device and arranged to analyze the digital data and provide a feedback code indicating the quality of the digital data points, wherein said processor is programmed to
      (i) assign each digital data point to one of a plurality of discrete compartments based on the position value of the data point, each compartment corresponding to a unique location on the object and comprising zero, one, or more digital data points;
      (ii) determine a quality value for each of said compartments based on the quality of the digital data points assigned to that compartment and assign to each compartment a feedback code representing said quality value; and (iii) transmit said feedback code to the output device.

2. An apparatus of claim 1, wherein said output device is a cathode ray tube.

3. An apparatus of claim 1, further comprising a memory arranged to store the digital data points.

4. An apparatus of claim 1, wherein said input probe comprises an indentation stiffness transducer, an ultrasound transducer, a temperature transducer, or an elevation transducer.

5. The apparatus of claim 1, wherein said feedback code is a visual code.

6. The apparatus of claim 1, wherein said feedback code is color.

7. The apparatus of claim 1, wherein said feedback code is a machine-readable control signal.

8. The apparatus of claim 1, wherein said property is elevation.

9. The apparatus of claim 8, wherein said input probe is an elevation transducer.

10. The apparatus of claim 8, wherein said elevation is of a structure within the object, and said input probe is an ultrasound transducer.

11. The apparatus of claim 1, wherein said probe is an indentation stiffness transducer.

12. The apparatus of claim 1, wherein said probe is a temperature transducer.

13. The apparatus of claim 1, wherein prior to transmitting the feedback code to the output device, the processor is further programmed to:

generate and assign new digital data points to each compartment comprising a feedback code indicating an unacceptable quality value, said new data points corresponding to sample points on the object at a location corresponding to said compartment;

determine a new quality value for each compartment to which new digital data points have been assigned and assign to each compartment a feedback code representing said new quality value; and repeat said generating and determining steps until all compartments are assigned a new feedback code indicating an acceptable quality value.

14. The apparatus of claim 13, wherein the feedback code transmitted to the Qutput device is in the form of a three-dimensional topography representing the property of the object.

15. A computer program for analyzing the quality of sampled data points representing a property of an object and generating a feedback code indicating the quality of the sampled data points, said program residing on a computer-readable medium and comprising instructions for causing a processor to:

(a) obtain digital data points representing a plurality of sample points on the surface of the object, each digital data point comprising a property value and a position value corresponding to a particular sample point;

(b) assign each digital data point to one of a plurality of discrete compartments based on the position value of the data point, each compartment corresponding to a unique location on the object and comprising zero, one, or more digital data points;

(c) determine a quality value for each of said compartments based on the quality of the digital data points assigned to that compartment and assign to each compartment a feedback code representing said quality value; and (d) transmit said feedback code to an output device.

16. The computer program of claim 15, wherein said feedback code is a visual code.

17. The computer program of claim 16, wherein said feedback code is color.

18. The computer program of claim 15, wherein said feedback code is a machine-readable control signal.

19. The computer program of claim 15, wherein prior to transmitting the feedback code to the output device, the program further causes the processor to:

generate and assign new digital data points to each compartment comprising a feedback code indicating an unacceptable quality value, said new data points corresponding to sample points on the object at a location corresponding to said compartment;

determine a new quality value for each compartment to which new digital data points have been assigned and assign to each compartment a feedback code representing said new quality value; and repeat said generating and determining steps until all compartments are assigned a feedback code indicating an acceptable quality value.

20. The computer program of claim 19, wherein the feedback code transmitted to the output device is in the form of a three-dimensional topography representing the property of the object.

* * * * *